Figure 1:

United States Patent [19]

Nunberg et al.

[11] Patent Number: 5,324,664

[45] Date of Patent: Jun. 28, 1994

[54] HERPES VIRUS THYMIDIEN KINASE-ENCODING DNA

[75] Inventor: Jack H. Nunberg, San Carlos, Calif.; Leonard E. Post, Ann Arbor, Mich.; Teresa Compton, Madison, Wis.; Erik A. Petrovskis, Ann Arbor, Mich.

[73] Assignee: The Upjohn Company, Kalamazoo, Mich.

[21] Appl. No.: 7,392

[22] Filed: Jan. 21, 1993

Related U.S. Application Data

[63] Continuation of Ser. No. 646,625, Jan. 28, 1991, abandoned, which is a continuation of PCT/US89/03289, Aug. 2, 1989, which is a continuation-in-part of Ser. No. 379,041, Jul. 12, 1989, abandoned, which is a continuation-in-part of Ser. No. 230,158, Aug. 8, 1988, abandoned.

[51] Int. Cl.$^5$ .................. C12N 15/86; C12N 15/38; A61K 45/00

[52] U.S. Cl. ................. 435/320.1; 435/69.1; 435/235.1; 435/172.1; 435/172.3; 536/23.1; 536/23.72; 536/24.1; 530/350; 424/93 A

[58] Field of Search ............ 435/69.1, 172.3, 235.1, 435/320.1, 236; 424/93; 530/350; 536/23.1, 23.72, 24.1

[56] References Cited

U.S. PATENT DOCUMENTS

| | | | |
|---|---|---|---|
| 4,514,497 | 4/1985 | Kit et al. | 435/235.1 |
| 4,683,202 | 7/1987 | Mullis | 435/91 |
| 4,703,011 | 10/1987 | Kit et al. | 435/236 |

FOREIGN PATENT DOCUMENTS

| | | |
|---|---|---|
| 0201184 | 12/1986 | European Pat. Off. |
| 0216564 | 4/1987 | European Pat. Off. |
| 226029 | 6/1987 | European Pat. Off. |
| 0251534 | 1/1988 | European Pat. Off. |
| WO87/04463 | 7/1987 | PCT Int'l Appl. |

OTHER PUBLICATIONS

Wohlgemuth, K., et al., J. Am. Vet. Med. Assoc., Pseudorabies Virus Associated with Abortion in Swine, 172:478–479 (1978).

Marchioli, C. C., et al., Am. J. Vet. Res., A Vaccine Strain of Pseudorabies Virus with Deletions in the Thymidine Kinase and Glycoprotein X Genes, 48:1577–1583 (1987).

Gaskell, R. M. and R. C. Povey, J. Comp. Path., The Dose Response of Cats to Experimental Infection with Feline Viral Rhinotracheitis Virus, 89:179–191 (1979) (Gaskell (1)).

Gaskell, R. M. and R. C. Povey, Res. Vet. Sci., Feline Viral Rhinotrachetis: Sites of Virus Replication and Persistence in Acutely and Persistently Infected Cats, 27:167–174 (1979) (Gaskell (2)).

Nasisse, M. P., et al., J. Vet. Intern. Med., Isolation of Feline Herpesvirus 1 from the Trigeminal Ganglia of Acutely and Chronically Infected Cats, 6:102–103 (1992).

R. F. Schinazi, C. C. Williams, M. E. Fritz and A. J. Nahmias, in the Human Herpersviruses, Elsevier, N.Y., 1981, pp. 681–682.

Proc. Natl. Acad. Sci, USA, vol. 81, Sep. 1984, (US) M.

(List continued on next page.)

Primary Examiner—Richard A. Schwartz
Assistant Examiner—David Guzo
Attorney, Agent, or Firm—James D. Darnely, Jr.; Gregory W. Steele; Sidney B. Williams, Jr.

[57] ABSTRACT

Methods for isolating thymidine kinase-encoding DNA of a herpes virus are described. These methods utilize degenerate primers based on regions of relatively conserved amino acid sequence in herpes virus thymidine kinase proteins to initiate a polymerase chain reaction which yields large amounts of the thymidine kinase-encoding DNA. The methods are illustrated in the isolation of the thymidine kinase gene of feline herpes virus, which can be used to construct recombinant thymidine kinase-negative feline herpes viruses for purposes of constructing live vaccines and expression vectors. In addition, the regulatory elements of the feline herpes virus thymidine kinase gene are useful in the construction of recombinant DNA vectors.

22 Claims, 2 Drawing Sheets

OTHER PUBLICATIONS

F. Shih et al. "Expression of Hepatitis B Virus S Gene by Herpes Simplex Virus Type 1 Vectors Carrying Alpha-and Beta-Regulated Gene Chimeras", pp. 5867–5870.

Chemical Abstracts, vol. 105, No. 23, (Dec. 8, 1986), (Columbus, Ohio, US) P. A. Rota et al., "Physical Characterization of the Genome of Feline Herpesvirus-1", see p. 136, abstract 203931p & Virology, 1986, 154(1), 168–79.

Journal of Virology, vol. 63, No. 8, Aug. 1989, American Soc. for Microbiology (US) J. H. Nunberg et al., "Identification of the Thymidine Kinase Gene of Feline Herpesvirus: Use of Degeneratie Oligonucleotides in the Polymerase Chain Reaction to Isolate Herpesvirus Gene Homologs", pp. 3240–3249.

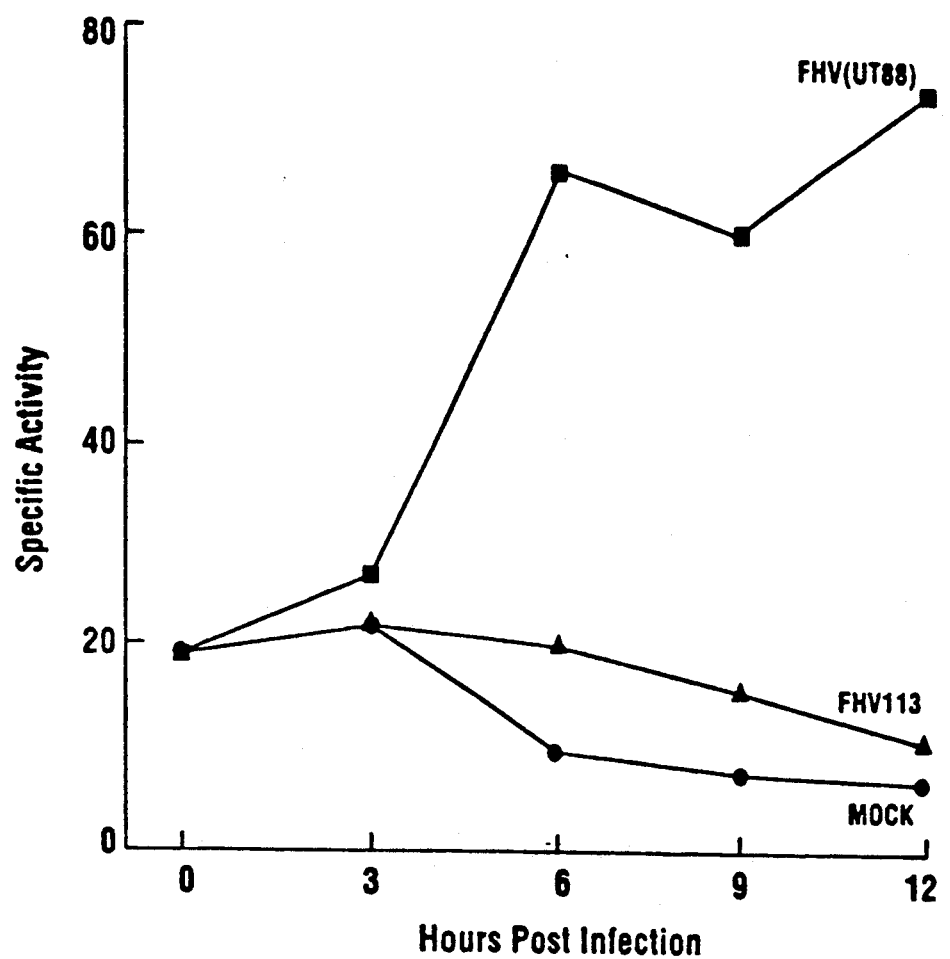

HERPES VIRUS THYMIDIEN KINASE-ENCODING DNA

CROSS-REFERENCE TO RELATED APPLICATIONS

This application is a continuation of Ser. No. 07/646,625, filed 28 Jan. 1991, now abandoned, which was a continuation of the international application PCT/US89/03289, filed 2 Aug. 1989, which is a continuation-in-part of Ser. No. 379,041, filed 12 Jul., 1989, abandoned, which was a continuation-in-part of Ser. No. 230,158, filed 8 Aug., 1988, abandoned.

SUMMARY OF THE INVENTION

In one aspect, the present invention provides methods for isolating and cloning thymidine kinase-encoding DNA from members of the herpesvirus family. These methods comprise mixing thymidine kinase-encoding DNA of a herpes virus with a mixture of primers, said mixture of primers containing primers that encode, in all variations possible due to the degeneracy of the genetic code, all variations of a first sequence of relatively conserved amino acids of herpes virus thymidine kinase proteins, and primers that encode, in all variations possible due to the degeneracy of the genetic code, sequences complementary to sequences that encode all variations of a second sequence of relatively conserved amino acids of herpes thymidine kinase protein; amplifying the thymidine kinase-encoding DNA by the polymerase chain reaction; and isolating the amplified DNA. The invention also provides mixtures of primers useful in practicing the method.

In a second aspect, the invention provides DNA compounds that encode the thymidine kinase (TK) of feline herpes virus (FHV), also known as feline viral rhinotrachetitis virus. These DNA compounds, which include recombinant DNA vectors that comprise TK-encoding DNA, are particularly useful in generating recombinant FHVs that can be used as vaccines and expression vectors. As used herein, "TK-encoding DNA" refers to DNA encodes a portion of the amino acid residue sequence of a herpes thymidine kinase and can include sequences that flank such DNA on a herpes virus genome.

In a third aspect, the invention provides methods for constructing thymidine kinase negative FHVs. These methods comprise constructing a recombinant DNA vector that encodes a non-functional FHV TK gene; transfecting an FHV-permissive host cell with a mixture of TK-positive FHV and the plasmid that encodes a non-functional TK gene; isolating the progeny virus; infecting an FHV-permissive host cell with said progeny virus to produce thymidine kinase-negative virus; and isolating said replicating TK-negative virus. The virus can be isolated by methods well known in the art, for example, by culturing the infected host cells under conditions where only thymidine kinase negative virus replicates. A portion of these TK-minus viruses will contain the plasmid TK-minus-encoding DNA recombined into the viral genome. The recombinant FHVs produced by the method are also an important aspect of the present invention.

Tymidine kinase negative herpesviruses can also be isolated by drug selection, e.g., 100 μg/ml thymidine orabinoside in the culture medium. These mutations can be spontaneous or mutagen induced. Preferably these mutations involve deletions and are made via recombinant DNA.

Thus, in a fourth aspect, the present invention provides FHVs that do not contain a functional TK gene, and so are referred to as "TK-negative" and "TK-minus" FHVs. Such TK-minus FHVs are useful as vaccines, because in comparison to wild-type FHV, a TK-minus FHV is attenuated in its ability to render an infected animal ill yet can still elicit an immune response that protects against further infections by wild-type FHV. In addition, the invention provides recombinant TK-negative FHVs that comprise an expression cassette inserted into the TK gene sequence of the FHV. Such an insertion renders the FHV TK-negative but, more importantly, also renders the FHV into an expression vector. As used herein, "expression cassette" refers to a recombinant DNA sequence that encodes a promoter operably linked to a coding sequence, such that when the expression cassette is present in an FHV-infected host cell, the promoter can drive transcription of an mRNA (e.g., that encoding feline leukemia virus (FeLV) envelope protein) that is capable of being translated into protein by the cell.

FIG. 1: Restriction Endonuclease Analysis of Recombinant FHV.

(A) EcoRI restriction endonuclease digestion of parental FHV UT88-1729 (1) and recombinant araT-resistant FHV-113 (2).

(B) The EcoRI-digested DNA visualized in panel A was transferred to nitrocellulose and tk sequences were identified by using a nick-translated hybridization probe comprising the 3′ portion of the FHV tk gene. The tk-containing 6.6 kb EcoRI fragment in the parental virus (1) is reduced by approximately 345 bp in the deletion-containing virus FHV-113 (2). Molecular size markers (HindIII-λDNA) are indicated. Several other EcoRI fragments which also do not comigrate in both viral DNAs map to the repeat regions of FHV (44); variation in the molecular size of these regions has been noted in unrelated experiments in which FHV is plaque-purified from a population.

FIG. 2: Results of Assay of tk Enzymatic Activity.

DETAILED DESCRIPTION OF THE INVENTION

The present invention provides a method for isolating any thymidine kinase-encoding DNA of any herpes virus. These methods comprise (a) mixing herpes virus DNA with a mixture of primers, said mixture of primers containing primers that encode, in all variations possible due to the degeneracy of the genetic code, all variations of a first sequence of relatively conserved amino acids of herpes virus thymidine kinase proteins, and primers that encode, in all variations possible due to the degeneracy of the genetic code, sequences complementary to sequences that encode all variations of a second sequence of relatively conserved amino acids of herpes thymidine kinase protein; (b) amplifying the thymidinekinase-encoding DNA by the polymerase chain reaction; and (c) isolating the amplified DNA.

The first step in these methods involves mixing herpes virus DNA with a mixture of primers. "Primers," as used herein, refers to oligonucleotides that can be extended by the action of a DNA polymerase in the polymerase chain reaction. The design of the primers useful in the methods of the present invention is dictated by two factors: (i) the primers must be amenable to use in the polymerase chain reaction; and (ii) the primers must be able to hybridize to a single-stranded DNA that either encodes thymidine kinase or is the complement to a single-stranded DNA that encodes thymidine kinase. Each of these factors is discussed in detail below.

The polymerase chain reaction is a well known technique, described in U.S. Pat. No. 4,683,202 and other applications and patents for amplifying DNA. Primers for use in the polymerase chain reaction are designed to be able to hybridize with at least one strand of the double-stranded target DNA sequence to be amplified. Briefly stated, the polymerase chain reaction involves the following steps. First, the double-stranded target sequence is denatured. Second, a first primer is annealed to one strand of the denatured target DNA while a second primer is annealed to the other strand of the denatured target DNA. The two primers anneal to the target DNA at sequences removed from one another and in orientations such that the extension product of one primer, when separated from its complement, can hybridize to the other primer. Once a given primer hybridizes to the target sequence, the primer is extended by the action of DNA polymerase. The extension product is then denatured from the target sequence, and the process is repeated.

In successive cycles of this process, the extension products produce in earlier cycles also serve as sites for DNA synthesis. Beginning in the second cycle, the product of amplification begins to accumulate at a logarithmic rate. This product is a double-stranded DNA molecule, one strange of which contains the sequence of the first primer, which is followed by the sequence of one strand of the target DNA, which, in turn, is followed by a sequence complementary to the sequence of the second primer. The other strand of the product is complementary to the first strand just described.

Several aspects of the polymerase chain reaction are important to note for purposes of the present invention. First, primers can be designed with convenient restriction enzyme recognition sequences located at or near the 5' end of the primer. In the formation of extension products in the polymerase chain reaction, new nucleotides are added beginning at the 3' end of the primer. These new nucleotides are added only if the 3' end of the primer is hydrogen-bonded to the target sequence, so the sequences that encode the restriction enzyme recognition sequence must be located at or near the 5' end of the primer. For example, one primer might contain a BamHI restriction enzyme recognition sequence at its 5' end, while the other primer might contain an EcoRI restriction enzyme recognition sequence at its 5' end. After amplification, the product would be digested with BamHI and EcoRI restriction enzymes and cloned into an appropriately cleaved cloning vector. The presence of such restriction enzyme recognition sites in the product greatly facilitates cloning.

Second, the target of amplification can be single-stranded DNA. Although the polymerase chain reaction procedure described above involves the assumption that the target was double-stranded, a single-stranded target sequence can serve as well in the amplification process. After the final cycle of amplification of a single-stranded target, the reaction mixture essentially contains a double-stranded target molecule consisting of the single-stranded target and its complementary strand, so successive cycles of amplification proceed as described above.

The second important factor in designing the mixture of primers used in the methods of the present invention is that the primers must be able to hybridize to DNA that encodes the thymidine kinase of any herpes virus. The thymidine kinase genes of known herpes viruses are quite diverged and contain only very short and interspersed regions of amino acid identity (see Kit, 1985, *Microbiol. Sciences* 2:369–375). For instance, pairwise comparison of the HSV1 TK (McKnight, 1980, *Nuc. Acid Res.* 8:5949) protein with that of pseudorabies virus (PrV, see U.S. Pat. No. 4,514,497) or varicella zoster virus (VZV, see Davison et al., 1986, *J. Gen. Virol.* 67:1759–1816) reveals only 7 colinear regions in which all 4 amino acids within my stretch of 4 amino acids are identical between pairs. The points of identity are not necessarily conserved between pairwise comparisons. Additional herpes virus TK genes that further illustrate this divergence include HSV-2 (Swain et al., 1983, *J. Virol.* 46:1045–1050), MaHV (Otsuka et al., 1984, *Virol.* 135:316–330), and IBR (EPO 226,029), Efforts to isolate the FHV TK gene via standard hybridization methods using the known TK genes as probes were not fruitful, because the divergence of TK proteins and the degeneracy of the genetic code renders such hybridization techniques too nonspecific.

The methods of the present invention, however, provide a way to isolate and clone any herpes thymidine kinase-encoding DNA. These methods utilize oligonucleotide primers that encode, in all variations possible due to the degeneracy of the genetic code, all variations of the very small regions of amino acid sequence homology between known herpes virus thymidine kinases. Although the number of primers in an amplification reaction designed to isolate TK-encoding DNA is quite large, only those primers that hybridize are amplified in the reaction. Thus, the methods of the present invention are quite specific in that the use of short, highly-degenerate oligonucleotides that encode (or are complementary to DNA that encodes) short, moderately conserved amino acid sequences requires that (i) two primers anneal; (ii) to opposite strands; and (iii) yield a product of the size expected. The methods of the invention are illustrated by the isolation of the feline rhinotracheitis virus TK gene. This virus, referred to herein as feline herpes virus (FHV) contains a TK gene never before isolated or characterized. The FHV TK gene was obtained using short, highly-degenerate oligonucleotide primers by the methods of the present invention.

Although the present invention is not limited to particular primers, because other regions of conserved amino acid sequence than those exemplified herein exist, the invention does provide preferred primers for use in the method for isolating TK-encoding DNA. Because these primers can contain non-homologous DNA at the 5' end of the primer (i.e., restriction enzyme recognition site-encoding DNA, as described above), and because the primers encode a relatively conserved amino acid sequence, the preferred primers of the invention are defined as comprising a coding sequence (or the complement thereof) for a relatively conserved amino acid sequence.

It should be noted that a given "conserved amino acid sequence" can consist of two or more sequences, and thus the methods of the invention refer to "all variations of a conserved amino acid sequence." For example, residues 55–60 (numbering of amino acid residues for purposes of designating conserved regions refers to the HSV 1 TK amino acid sequence) are relatively conserved within the herpes virus thymidine kinases, i.e., this region is not identical in every herpes virus thymidine kinase at each position in the sequence but is still recognizable as a region of homology. In constructing primers for such a conserved region for purposes of the present invention, however, one need only design the primers to encode, in every variation possible due to the degeneracy of the genetic code, each variation of the conserved sequence. The preferred primers of the invention are depicted in Table 1, below, by reference to the conserved amino acid sequences, some of which are variant as just described. The amino acid sequences are given in one-letter code, described in Table 2. The position of the amino terminal residue in the conserved sequence (relative to the HSV-1 TK) is indicated on the first line of Table 1. The virus in which a particular conserved sequence is found is indicated at the left side of each line. Because of the degeneracy of the genetic code, and because the method of the invention utilizes primers that encode all possible coding sequences for a conserved amino acid sequence (and the complementary strands of such coding sequences), the actual number of primers used in the method that encode a given conserved amino acid sequence is indicated in the line entitled "primer degeneracy." Finally, Table 1 also depicts the actual length of the portion of the primer that encodes the conserved sequence. In some cases, due to the variability of the nucleotide in the third position of a codon, this length can be one nucleotide shorter than the calculated three nucleotides per conserved amino acid.

TABLE 1

Primers for Isolating TK-encoding DNA

|  | 55 | 61 | 164 | 220 | 287 |
|---|---|---|---|---|---|
| HSV-1 | DGPHG | GKTT | DRHP | RPGE | DTLF |
| VZV | DGAYG | GKTT | DRHP | RPGE | DTLF |
| PrV | DGAYG | GKST | DRHP | RAGE | DTLF |
| MaHV | DGPHG | GKST | DRHA | RPGE | — |
| Primer length | 14 | 11 | 11 | 11 | 12 |
| Primer degeneracy | 256 | 112 | 48 | 196 | 96 |

TABLE 2

Amino Acid Abbreviations

| Amino acid | Three-letter abbreviation | One-letter abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The primers shown in Table 1 are used in pair wise combinations. For example, one could isolate a TK-encoding DNA by amplifying with a primer pair in which the first primer encodes the conserved amino acid sequence beginning at position 55 (as shown in Table 1, this first primer would be a mixture of primers that comprises sequences that encode DPGHG and sequences that encode DGAYG in all variations possible due to the degeneracy of the genetic code) and in which the second primer comprises sequences that are complementary to sequences that encode the conserved amino acid sequence beginning at position 220 (as shown in Table 1, this second primer is a mixture of primers that comprise sequences complementary to sequences that encode RPGE and sequences that encode RAGE in all variations possible due to the degeneracy of the genetic doe). The expected size of the product of amplification would be about 495 base pairs (bp) in length ($220-55 = 165$, $165 \times 3 = 495$). The amplification reactions can be carried out on Perkin-Elmer Cetus Instruments Thermal Cycler using the thermostable DNA polymerase of *Thermus aquaticus* in accordance with the manufacturer's protocol. In addition, reaction protocols for the polymerase chain reaction using a thermostable polymerase are described U.S. Pat. Nos. 4,683,193 and 4,683,202 and U.S. patent applications Ser. Nos. 063,647 (filed Jun. 17, 1987) and 899,513 (filed Aug. 22, 1986), all of which are incorporated herein by reference. In addition, methods for amplifying DNA using the DNA polymerase of *T. aquaticus* are described in Saiki et al., 1988, *Science* 239:487-491.

To silate the FHV TK-encoding DNA of the present invention, primer pairs as shown in Table 1 and including 5' extensions containing restriction endonuclease recognition sites (to facilitate subsequent cloning of the product of amplification) were used in the method of the present invention. The amplification reactions were carried out on a Perkin-Elmer Cetus Instruments Thermal Cycler using the thermostable DNA polymerase of *Thermus aquaticus* in substantial accordance with the manufacturer's protocol, except as follows. From 30 ng to 1 μg of FHV DNA (US-D strain of FHV, obtained from Niels Pedersen, University of California Veterinary School, Davis, Calif.) and 100 to 800 pmol of degenerate primers were used in each 50 μl reaction. The thermal cycling included an initial 5 cycles with an annealing step at 37° C.

One pairwise combination of primers yielded the expected product. This primer pair was designed to amplify the region between and containing the conserved sequences beginning at position 55 and 164 as depicted in Table 1. Thus, the primer pairs had the following sequences. The first primer was:

5'-TCAAAGCTTGAYGGNSCNYAYGG-3'

The second primer contained equal parts of the following primers:

5'-CTCGAATTCGSRTGNCGRTC-3' AND

5'-CTCGAATTCGSRTGYCTRTC-3',

In the sequence of the primers shown above, A is a deoxyadenine residue, T is a thymidine residue, C is a deoxycytidine residue, G is a deoxyguanine residue, N represents that the primer is a mixture of primers in which each of the four nucleotides can occur at the position indicated, R represents that the primer is a mixture of primers in which either of the two purine nucleotides (G and A) can occur at the position indicated, Y represents that the primer is a mixture of primers in which either of the two pyrimidine nucleotides (C and T) can occur at the position indicated, S represents that the primer is a mixture of primers in which either a G or C nucleotide can occur at the position indicated. Those skilled in the art will note that the first primer encodes a HindIII restriction enzyme recognition sequence (5'-AAGCTT-3') near the 5' end and that the second primer encodes an EcoRI restriction site (5'-GAATTC-3') at the 5' end.

The expected product from the primer pair described above had a length of about 350 bp (164−55=109, 109×3=327), and after the amplification reaction mixture was digested with restriction enzymes EcoRI and HindIII, the reaction mixture was loaded onto an acrylamide gel and subjected to electrophoresis. The approximately 350 bp product was excised form the gel and ligated with EcoRI-HindIII-digested BlueScript plasmid vectors (BlueScript is a tradename of Stratagene Corporation, 3770 Tansey Street, San Diego, Calif. 92121, and the vectors were used in substantial accordance with the manufacturer's protocol). The recombinant plasmids were sequenced to confirm that the approximately 350 bp EcoRI-HindIII restriction fragment encoded FHV thymidine kinase. This determination was made by comparing the amino acid sequence encoded by the coding sequence to that of other known herpes virus thymidine kinase proteins, which, although too divergent for cloning by hybridization are similar enough that such a determination is practicable. The approximately 350 bp fragment was then used to isolate the entire FHV TK gene from genomic libraries of FHV by labeling the 350 bp fragment, contacting the labeled fragment which the library under hybridizing conditions, and isolating the clones in the library that hybridized to the fragment. In this manner, the entire TK gene was isolated on two plasmids. The first, designated pTK3.8 is a 3.8 kg SalI-HindIII restriction fragment of FHV strain UC-D cloned into a Bluescript vector (purchased from Stratagene, La Jolla, Calif.), and the second, designated pTK5.4deltaBam is a 1.7 kb HindIII-BamHI restriction fragment of FHV strain UC-D cloned into a Bluescript vector.

The DNA sequence of the FHV TK gene was determined and is set forth below. Those skilled in the art recognize that there can be difficulty in interpreting DNA sequencing gels and that the sequence depicted below may differ from the actual sequence in a few nucleotide positions. However, using the methods of the invention, one can isolate any herpes virus TK-encoding DNA sequence. In addition, the present invention allows the position of the TK gene to be identified to a particular restriction fragment of the feline herpes virus genome. Rota et al., 1986, *Virol.* 154:168-179, reported a restriction map of a feline herpes virus that contains a SalI restriction fragment about 20 kilobases (kb) in length. This restriction fragment, termed the Sal A fragment, contains the feline herpes virus TK gene. Most feline herpes viruses are substantially homologous to this reported virus, which enables one of skill in the art to isolate the TK-encoding DNA compounds of the present invention merely by cloning the appropriate restriction fragment. The sequence is numbered to facilitate description of the sequence; the numbers appear at the left-hand side of the sequence. Only the coding strand of the sequence is depicted. Underlines portions of the sequence are described on the line above. "N" represents that the nucleotide in the designated position might be either A, G, T, or C.

Nucleotide Sequence of the Thymidine Kinase Gene of Feline Herpes Virus, Strain UC-D

```
  1 5'-GTATAACCAC AGATCTGTAT GTTCAACCTC ACGACGTTGA TGTCTTACTA
 51    GTGTATCCAT ATTTTGAAAA CGACACGTTT TCAGCTCAAT TAGAAAACAT
101    ATACCACCCC CTTCTCCCTC AAATTGTATA GTACATACAC AATCAGTCGG
151    CGACGACCCA AGTTAACCTC ACATGCTAGG TACACGCCCT TAGCCTTTTT .
                                                         CAAT box
201    AAGAGACTCT GCGGATACAG AGCCGCCCAA TAAACACTCG AGTCGGTCGG
                                                         TATA box
251    TATATACTCC ACTCGCAGAG GTCGAGGATA TATCGCGCTT GAGGACAGCA
301    TAAAAGCGAT TGTGGNATCG AATTCCAGCC CGGAGCCTCA ATCCGACACT
                                                start of coding sequence
351    GCGTCGTTGT TCACGTTTCA TCATACACAG ATCAGACGAT GGCGAGTGGA
401    ACCATCCCCG TTCAGAATGA AGAGATTATT AAATCACAGG TGAATACTGT
451    CCGCATTTAC ATAGATGGTG CCTATGGAAT AGGTAAGAGT TTAACGGCGA
501    AGTACCTGGT CAGAGCGGAT GAAAATCGAC CGGGATATAC TTACTACTTC
551    CCAGAACCAA TGCTATACTG GCGTAGTCTC TTTGAAACTG ATGTTGTCGG
601    TGGTATCTAT GCCGTCCAGG ACCGGAAACG ACGTGGTGAA TTATCAGCTG
651    AAGATGCTGC CTATATCACC GCCCACTATC AAGCAAGATT TGCCGCACCA
701    TACCTTCTTT TACATTCCAG ACTATCCACA ATAACAGGAT ATCAGAAAGT
751    TGTATGTGAG GAACACCCCG ACGTGACCCT AATCATAGAT AGACACCCTC
801    TCGCCTCTCT GGTCTGTTTC CCACTCGCAA GATATTTTGT GGGTGATATG
```

-continued
Nucleotide Sequence of the Thymidine Kinase Gene of Feline Herpes Virus, Strain UC-D

```
 851  ACTCTTGGGT CTGTACTTAG TCTAATGGCA ACACTTCCAC GAGAACCTCC
 901  TGGTGGAAAT CTAGTTGTAA CAACCTTGAA TATCGAGGAA CATTTGAAGC
 951  GTCTCAGGGG ACGCTCAAGA ACCGGAGAAC AGATAGACAT GAAGCTAATT
1001  CACGCACTAC GCAATGTATA TATGATGTTG GTACATACTA AGAAATTTTT
1051  AACAAAAAAT ACTAGTTGGC GTGATGGGTG GGGGAAGCTT AAAATTTTCT
1101  CCCACTATGA ACGGAATAGG CTCGTGGAAA CTACAATAGT TTCCGATTCG
1151  ACGGAGTCAG ATTTATGTGA CACATTATTC AGTGTTTTCA AAGCCCGGGA
1201  GCTCTCCGAC CAAAATGGAG ATCTACTTGA CATGCATGCA TGGGTCCTCG
1251  ATGGACTTAT GGAAACCCTC CAAAATTTAC AGATCTTTAC TTTAAATCTG
1301  GAAGGAACCC CTGATGAATG TGCCGCCGCC TTGGGAGCAC TGAGACAAGA
1351  TATGGATATG ACATTTATAG CCGCATGTGA TATGCACCGT ATAAGTGAAG
              end of coding sequence
1401  CCTTGACGAT ATACCATTAA ACATTAGTGG TGTTCCCTAT TACCCCCCTG
1451  TGGTGAATGT GTGGAGGTCA GGGGATAATT GTATAATGAC CATCGTTTCA
           poly A
1501  TGAATAAAAT AACCGTGTGT GATGTGGATG TATTCATTAA TTGAATTTCT
1551  CTTCCGGTTT TAGATCTTTA TAAGCGTAAA ACTGGTGTTT TAAATCCAAG
1601  AGCCGGGTTC TTTGGAGGTT GGTCACATCA TCGCCACAGC CCGTGGATTC
1651  AAGCAATCTT ATGATGTGTT TGATAATATA CCTATCGATA TTCCTGATCA
1701  TTGTATCGAG GATGTTGACT GGTTACCGAT GATGGATAGA CCTGATGAGG
1751  TGGCTGG-3'
```

The TK-encoding DNA sequence shown above, although isolated by the method of the present invention, can be constructed by synthetic means, i.e., by use of an automated DNA synthesizer, well known in the art. This TK-encoding DNA sequence is an important aspect of the present invention, as well as recombinant DNA vectors that comprise the sequence. In addition, the TK gene sequence shown above will be homologous to other TK-encoding DNA sequences of other FHVs, if other FHVs with a different TK-encoding DNA sequence exist. There may be a number of different FDHV strains that may differ from one another only in a minor way. These FHV variants may encode thymidine kinase proteins that differ from the FHV TK protein encoded by the TK gene of the present invention in some way; however, such variations will occur in less than 10% of the amino acid residue positions. Such variant genes can be readily located by a variety of methods, including hybridization with the TK-encoding DNA of the present invention and comparison of genetic maps to locate analogous TK-encoding regions. Thus, the present invention provides TK-encoding DNA from any FHV.

The TK gene sequence depicted above contains a promoter (a sequence that includes a CAAT region and TATA box, which can include sequences upstream of the CAAT region and downstream to about the start of the coding sequence), coding sequence, and poly A signal. The promoter and poly A signal are important regulatory elements that, though the use of recombinant DNA technology, can be used to construct recombinant genes that drive expression of any desired gene product. Thus, the promoter and poly A portions of the FHV TK gene are also important aspects of the present invention.

The coding sequence of the TK gene encodes a thymidine kinase with the following amino acid residue sequence shown below. The sequence is listed from amino to carboxy terminus.

```
  1 MASGTIPVQN  EEIIKSQVNT  VRIYIDGAYG  IGKSLTAKYL  VRADENRPGY
 51 TYYFPEPMLY  WRSLFETDVV  GGIYAVQDRK  RRGELSAEDA  AYITAHYQAR
101 FAAPYLLLHS  RLSTITGYQK  VVCEEHPDVT  LIIDRHPLAS  LVCFPLARYF
151 VGDMTLGSVL  SLMATLPREP  PGGNLVVTTL  NIEEHLKRLR  GRSRTGEQID
201 MKLIHALRNV  YMMLVHTKKF  LTKNTSWRDG  WGKLKIFSHY  ERNRLVETTI
251 VSDSTESDLC  DTLFSVFKAR  ELSDQNGDLL  DMHAWVLDGL  METLQNLQIF
```

301 TLNLEGTPDE CAAALGALRQ DMDMTFIAAC DMHRISEALT IYH

Those skilled in the art recognize that due to the degeneracy of the genetic code, a very large number of DNA sequences can be constructed that encode the thymidine kinase of the structure shown above. These DNA sequences are equivalent to the FHV TK-encoding DNA of the present invention.

The FHV TK gene is useful in the construction of infectious TK-minus FHV for use as attenuated FHV (feline rhinotracheitis virus) vaccines. The invention provides methods for constructing recombinant FHVs that comprise constructing a recombinant DNA vector that encodes a non-functional FHV TK gene; transfecting an FHV-permissive host cell with a mixture of TK-positive FHV and the plasmid that encodes a non-functional TK gene; isolating the progeny virus; infecting a feline herpes virus-permissive host cell with said progeny virus to produce thymidine kinase-negative virus; and isolating said replicating TK-negative virus. The resulting TK-negative virus will contain a mixture of virus, only a portion of which are rendered TK-negative as a result of recombination with the plasmid-borne TK sequences. The remaining portion of TK-minus viruses is a result of spontaneous mutation to the TK-minus state. The recombinant FHVs produced by the method are also an important aspect of the present invention.

A number of TK-minus herpes viruses are known that show reduced virulence and so can be used as attenuated virus vaccine (see, e.g., European Patent Publication 226 029; and U.S. Pat. No. 4,703,011 which describe bovine herpesviruses type 1 which fail to produce any functional tymidine kinase as a result of deletion in the thymidine kinase gene. Also this patent refers to other herpes viruses). Before the present invention it was not known whether it was possible to make a viable thymidine kinase negative feline herpesvirus, how to make such a virus, whether such a virus would be virulent or avirulent in cats, or whether such a virus would produce a protective immune response in cats. The fact that tk negative pseudorabies virus is virulent in cats teaches against the idea that tk negative herpesviruses are avirulent in cats. It is only as a result of the instant invention that it has in fact been demonstrated that tk minus FHVs are avirulent and are protective vaccines. To obtain such an FHV TK-minus vaccine to immunize cats and other susceptible animals against infection by wild-type FHV, one need construct a recombinant vector that encodes a non-functional FHV TK-gene but retains sufficient homology to the wild-type FHV TK gene and flanking sequences for recombination. Then, the non-functional TK gene is recombined with TK-positive FHV DNA and TK-negative recombinants are selected. It is important to note that a "non-functional" TK gene includes a segment of FHV genomic DNA that is colinear with the FHV genome except for a deletion or insertion (e.g., insertion of an expression cassette, as described below) or point mutation that renders the TK gene inoperative.

In a variation on this theme, the non-functional TI gene is modified to also include an expression cassette. In the preferred embodiment, this expression cassette will drive expression, when present in the animal immunized with the recombinant virus, of a protein that will induce immunity to other infectious agents. For instance, feline leukemia virus (FeLV) is an infectious agent for which immunizing vaccines are needed. The FHV TK-minus recombinant viruses of the present invention are readily modified to encode FeLV proteins, such as the envelope, pol, or gag proteins, that, when expressed in the immunized animal, will render the animal resistant to FeLV. Of course, the infectious recombinant FHVs of the present invention can express other genes for use in cats, cat cells, or other cells or animals susceptible to FHV infection. For example, the recombinant TK-minus FHVs can be used as vaccines against feline infectious peritonitis (FIP)virus, calicivirus, rabies virus, feline immunodeficiency virus (FIV), feline parvovirus (panleukopenia virus), and feline Chlamydia; and as generalized expression vectors, i.e., to correct genetic defects or to provide additional growth, merely by choice of the appropriate expression cassette.

To obtain recombination and insertion of foreign sequences within the FHV genome, it is necessary to flank the inserted sequence with FHV sequences; in the case of targetted insertion within the FHV TK gene, it is necessary to insert the foreign gene or expression cassette into the FHV TK gene and to flank this insert with (50–5000 bp) colinear sequence including and/or surrounding the FHV TK gene. Insertion of an expression cassette within the FHV TK gene will generate a recombinant TK-minus FHV suitable as an attenuated live FHV vaccine.

The plasmids described below contain expression cassettes that can be inserted into the TK gene of the present invention; the resulting construct can be recombined with FHV to yield and FHV TK-minus recombinant virus illustrative of the invention. These expression cassettes demonstrate the ability of a variety of herpes virus promoters to drive expression of any protein, as illustrated by a beta-galactosidase marker protein, which is easily detected by chromogenic assays, in FHV-infected cells. Such promoters include the herpes simplex alpha-4 promoter (a4), which can be isolated from plasmid pRB403, described by Roizman et al., 1982, Proc. Natl. Acad. Sci. 79:4917–4921, on a PvuII-BamHI restriction fragment; the cytomegalovirus immediate early promoter (CMVIE), which can be isolated from plasmid pCMV5027, described by Schaffner et al., 1985, Cell 41:521–530, on a Sal I-SacII restriction fragment with minor repair (the Sal I site is from vector polylinker in pCMV5027, and is where a Pst I site exists upstream from the CMV promoter); and the FHV TK promoter described above, which can be isolated on a Sal I-EcoRI restriction fragment (the EcoRI site is about 100 bp upstream of the ATG that starts the coding sequence).

Each of these promoters were cloned into appropriate sites in the beta-galactosidase-encoding but promoter-less plasmid pON1, described by Spaete et al., 1985, J. Virol. 56:135–143. Transfection and assay for beta-galactosidase expression in FHV-infected CRFK cells (available from the American Type Culture Collection, 13301 Parklawn Drie, Rockville, Md. 20852-1776, under the accession number ATCC CCL 94) or HSV1-infected Vero cells from the ATCC were essentially as described by Spaete et al., 1985, J. Virol. 56:135–143, incorporated herein by reference. The results are depicted in Table 3, below.

TABLE 3

| Beta-Galactosidase Specific Activity (nmol/min/mg) | | | | |
|---|---|---|---|---|
| Virus | None | HSV | None | FHV |
| Promoter | α4 | α4 | α4 | α4 |
| Cell | Vero | Vero | CRFK | CRFK |
| Activity | 5.1 | 31 | 10.3 | 28 |
| Virus | None | HSV | None | FHV |
| Promoter | FHVtk | FHVtk | FHVtk | FHVtk |
| Cell | Vero | Vero | CRFK | CRFK |
| Activity | not tested | not tested | 1.2 | 2.8 |
| Virus | None | HSV | None | FHV |
| Promoter | CMVIE | CMVIE | CMVIE | CMVIE |
| Cell | Vero | Vero | CRFK | CRFK |
| Activity | 32 | 106 | 35 | 100 |

Thus, all expression cassettes are believed to be active in FHV-infected cat CRFK cells, and the highest expression of β-galactosidase was from the CMF IE promoter. The highest activity reported in mock-transfected cells was 0.6 nmol/min/mg. Replacement of the beta-galactosidase coding sequence with, e.g., the FeLV envelope protein coding sequence, will produce an expression cassette that can be used as described above to construct an attenuated virus of the present invention that is suitable for use in vaccination against FHV and FeLV.

Other promoters that drive expression in FHV-infected cells can also be used in the construction of expression cassettes for use in the recombinant FHVs of the present invention. These include promoters derived from other herpes viruses, especially strongly-expressed promoters, as well as those derived from FHV, especially the major capsid protein gene promoter and the glycoprotein promoters (e.g., gB or gC homologues).

A number of plasmids containing the expression cassettes descried in Table 3 inserted into the FHV TK gene of the present invention were constructed. These plasmids are referred to as insertion vectors, because when recombined with TK-positive FHV, the plasmids will insert the expression cassette-containing TK gene into the TK-positive FHV to yield a TK-minus FHV that contains the expression cassette. Thus, insertion vector pTC4 contains an expression cassette composed of the CMV IE promoter positioned to drive expression of beta-galactosidase.

Insertion plasmid pTC4 was transfected, together with infectious FHV genomic DNA, into CRFK cells using methods similar to those developed by Roizman et al. in the herpes simples virus system (see Roizman et al., 1981, *Cell* 25:227-232; Roizman et al., 1981, *Cell* 24:555-565; Roizman et al., 1980, *Cell* 2:243-255; Roizman et al., 1982, *Dev. Biol. Standardization* 52:287-304; European Patent Publication 074,808; Roizman et a., 1985, *Science* 229:1208-1214) and by Lose et al., 1987, *Proc. Natl. Acad. Sci.* 84:3896-3900, in the varicella zoster virus system.

Infectious FHV DNA can be generated by infecting subconfluent monolayers of CRFK cells with FHV at low multiplicity of infections. Cells are harvested when the cytopathic effect (CPE) has reached maximum. Cytoplasmic viral DNA is obtained by first removing cell nuclei by NP-40 extraction and treating the cytoplasmic fraction with 100 μg/ml proteinase K and 0.2% SDS (sodium dodecyl sulfate) for two hours at 37° C. The viral DNA is purified by sodium iodide density ultracentrifugation. The DNA is then dialyzed and used directly in transfections to generate recombinants.

To generate virus recombinants, the plasmid containing the expression cassette inserted into the TK gene is cotransfected with FHV DNA using the calcium phosphate precipitation method (Graham and vander Eb, 1973). 1 μof plasmid DNA and 3 μg of FHV DNA are coprecipitated in 125 mM $CaCl_2$ and 1 X Hepes buffered saline (HBS) at room temperature for 30 minutes. This precipitate is added to a 25 $cm^2$ subconfluent dish of CRFK cells with 5 ml of DMEM medium supplemented with 10% fetal calf serum (FCS). After four hours, the cells are washed with DMEM (10% FCS) and incubated in 15% glycerol, 1HBS for six minutes. The cells are washed and incubated in DMEM (10% FCS) until complete CPE is detected. The virus stock is harvested by freeze-thawing and sonication. Plaques are isolated by incubation in Medium 199 supplemented with 0.5% agarose, 1% FCS, 100 μg/ml thymine arabinoside (araT). X-gal is added (300 μg/ml) after 48 hours if beta-galactosidase activity is to be detected. Blue plaques develop three days post infection and are picked, transferred to 1 ml of Medium 199 (1% FCS), sonicated and used to infect monolayers of CRFK cells. Tis process of plaque purification is repeated three times to generate a homogenous viral stock.

Progeny virus were harvested and plaqued on CRFK cells in the presence of 100 ug/ml araT, a thymidine analogue that selects for TK-minus virus. Plaques were stained for beta-galactosidase activity by including the chromogenic indicator X-gal (5-bromo-4-chloro-3-indoyl-beta-D-galactopyranoside) in the agar overlay, as described by Spaete et al., 1987, *Proc. Natl. Acad. Sci.* 84:7213–7217. Approximately five percent (5%) of the araT-resistant, TK-minus FHV plaques stained for beta-galactosidase expression developed the blue color indicative of the presence of beta-galactosidase activity on X-gal indicator plates. These viruses are plaque-purified as described above. These viruses express both the araT-resistant (TK-minus) and beta-galactosidase-positive phenotypes. The insertion of the CMV IE promoter/eta-galactosidase expression cassette within the TK gene of the FHV genome is confirmed by Southern analysis of FHV genomic DNA. This virus can be used as an attenuated FHV vaccine (and beta-galactosidase expression vector) for cats. Replacement of the beta-galactosidase gene with the envelope gene of FeLV subgroup A within a TK-based insertion plasmid will yield, via similar methods, a recombinant TK-minus FHV of the present invention that can drive expression of the FeLV envelope gene product in cats. Such a recombinant FHV can be used as a vaccine for FeLV and FHV.

Convenient methods other than TK-minus selection to select the desired recombinant virus are feasible as a result of work described in this application. As has been done with recombinant vaccinia virus vectors (Chakrabarti et al., 1985, *Mol. Cell. Bio.* 5:3403–3409), a cassette capable of driving expression of beta-galactosidase can be co-inserted with another heterologous protein expression cassette into, for example, the TK gene, and these two genes can be together transferred into the viral genome. Recombinant viruses are then readily screened by virtue of their staining with the beta-galactosidase specific chromogenic reagent X-gel. Thus, for example, the CMV IE promoter/beta-galactosidase expression cassette can be inserted along with the FHV TK promoter/FeLV envelope gene product expression cassette into the FHV TK gene as described above, and recombinant viruses could be isolated by staining with X-gal.

If a TK-positive phenotype is desired in a recombinant TK-minus virus in which the heterologous expression cassette is inserted within the TK gene, then a functional FHV TK gene can be inserted elsewhere in the genome. As current anti-herpes virus therapy acts through a functional TK gene, it may be desirable to include a functional TK gene in the vaccine strain. This has not been done in the case of currently approved recombinant TK-minus pseudorabies virus vaccines (TechAmerica, Omni-Vac PRV). Attenuation by virtue of the TK-minus phenotype can be obtained by interrupting the FHV TK gene, regardless of the site of integration of the expression cassette. In addition, the parental FHV virus can itself be attenuated through other means, independent of the TK gene. Conventionally produced attenuated FHV viruses are in current use as FHV vaccines.

The use of FHV as a vector for vaccination in cats is preferred to any other virus, including vaccinia virus. FHV replicates well in cats, and attenuated viruses are in current use in vaccination. Furthermore, the virus host-range is restricted to felines—this virus is not presently known to infect other animals and humans and thus does not pose the same public health concerns as vaccinia virus (which is considered a class 2 pathogen, because vaccination with the virus for smallpox immunization was ceased several years ago).

Recombinant virus construction: A bacterial plasmid containing a deletion in the identified FHV tk gene was constructed using standard molecular cloning techniques. This plasmid and FHV strain UT88-1729 DNA were cotransfected into CRFK cells by using the calcium phosphate precipitation method described in Graham, F. L. and A. J. vander Eb., 1973, "A New Technique for the Assay of Infectivity of adenovirus 5 DNA", Virology 52: 446–467. Progeny virus was harvested when full cytopathic effect was evident and recombinant FHV plaques were isolated in the presence of araT. The desired recombinant virus was identified by restriction endonuclease analysis.

Construction of recombinant tk-FHV:

FeLV Envelope Insertion

| EcoRI | (EcoRV) | | | (HindIII) | |
|---|---|---|---|---|---|
| 0.4 | 1.2 | 2.1 | 1.5 | 0.3 | |
| TK | PCMV | FeLV gp85 | lacz SV40 poly A enhancer | TK | |

The diagram above represents an FHV-gp85 recombinant virus (FHV114). The sequence from the EcoRV site to the HindIII site in the thymidine kinase gene has been deleted, attenuating the virus. An expression cassette including the FeLV gp85 gene has been inserted. The promoter in this cassette is from the CMV immediate early gene (Thomsen et al, PNAS 81:659–663)1984). The polyadenylation signal was isolated from pON1 [Spaete and Mocarski, J. Virol. 56:135–143 (1985)]. CRFK cells infected with this virus synthesize FeLV gp85.

To obtain genetic and biochemical confirmation that the identified tk gene encodes FHV tk, we constructed a recombinant FHV in which the tk coding sequence had been modified to delete the nucleoside binding domain of the deduced tk protein.

The bacterial plasmid ptkΔEcoRV-Hind III (pGC113) contains the entire FHV tk gene and flanking regions (from the SalI site to the proximal BamHI site), but lacks coding sequences between the ECoRV and HindIII sites. A synthetic oligonucleotide polylinker was used to join these sites in the plasmid construction. The resulting protein is predicted to contain a novel serine residue inserted at the site of the glycine$_{117}$ to lysin$_{234}$ deletion.

This mutation was introduced into FHV by using calcium phosphate co-precipitation techniques to obtain homologous recombination between plasmid and herpesvirus genomic sequences. The plasmid ptΔEcoRV-HindIII and FHV strain UT88-1729 genomic DNA were cotransferred into CRFK cells and progeny virus was harvested and plaqued onto CRFK cells in the presence of 100 μg/ml thymidine arabinoside (araT) to select for recombinant tk$^-$ virus. Previous studies had shown this thymidine analogue to provide stringent selection against the replication of tk$^+$ FHV, R. F. Schinazi, C. C. Williams, M. E. Fritz and A. J. Nahmias, in the Human Herpesviruses, Elsevier, New York, 1981, pp. 681–682, and we have used this selection method to isolate spontaneous tk$^-$ FHV. AraT-resistant viruses were screened by restriction endonuclease analysis for the presence of the EcoRV-HindIII deletion. All araT-resistant viruses examined contained the expected deletion. One virus was further plaque purified and was designated FHV-113. As expected, the 6.6 kb EcoRI fragment containing the FHV tk gene is reduced in size by approximately 345 pb in FHV-113 (FIG. 1).

The araT-resistant phenotype of FHV-113 was shown to be attributable to a defect in tk by direct enzymatic assay of tk activity in extracts of infected cells. Results of these assays (FIG. 2) confirm the araT-resistant FHV-113 to be deficient in tk enzymatic activity. Thus, genetic and biochemical analysis supports the assignment based on the deduced amino acid sequence, and establishes that the identified gene encodes FHV tk.

EXAMPLE 1

Construction of a tk Deletion of FHV-1

The FHVΔ113 virus was constructed as follows. pTK 3.8, described above, contains the 3.8 kb SalI/HindIII fragment containing the N-terminal coding sequence of the tk gene. A derivative of this plasmid, tk3.8ΔEcoRI was obtained by deletion of sequences between the EcoRI site in the TK promoter and in the Blue Script KS polylinker.

The plasmid pTK5.4, described earlier, contains the 5.4 kb HindII/EcoRI fragment containing the C-terminal coding region of the tk gene and the glycoprotein H gene. p5.4ΔBamHI was constructed by deletion of the sequences from the BamHI site just downstream from tk to the BamHI site in the Blue Script SK polylinker.

pGCIII was assembled by ligating the ApaI/EcoRI fragment from ptk3.8ΔEcoRI containing the region upstream from the tk gene, plus the HindIII/AApaI fragment from ptk5.4ΔBamHI, using a synthetic oligonucleotide to link the HindIII and EcoRI cleavage sites. The resulting sequence between the EcoRI and HindIII sites is GAATTCGCGGCCGCAAGCTT.

The insertion vector pGC113 was derived from pGCIII by inserting an EcoRI/EcoRV fragment containing the 5'-end of the tk gene (bases 321–740 in the above DNA sequence), between the EcoRI and HindIII sites of pGCIII, using a synthetic oligonucleotide to linker the EcoRV and HindIII sites. The resulting sequence between the EcoRV and HindIII sites was GGATCCAAGCTT, to regenerate the HindIII site and create a novel BamHI site.

The parent of the tk deletion virus was a highly virulent strain, UT88-1729 (obtained from Malcolm Martin, University of Tennessee Veterinary Teaching Hospital, Knoxville, Tenn.). Viral DNA was prepared from sodium dodecyl sulfate-proteinase K treated cytoplasmic nucleocapsids by the method of Walboomers and Scheggett (Virology, 74, 256–258, 1976), and described above. Using the transfection protocol described above, FHV DNA plus pGC113 DNA was transfected into CRFK cells. A thymidine kinase negative plaque was isolated by thymidine arabinoside selection.

The resulting virus, designated FGH-113, contains a tk deletion. Its DNA, analyzed by restriction enzyme EcoRI, is shown in FIG. 1 and its tk⁻ phenotype is demonstrated in FIG. 2.

EXAMPLE 2

Construction of a FHV Expressing FeLV gp85

The plasmid pON1 contains an *E. coli* beta galactosidase gene and SV40 polyadenylation signal (Spaete, et al., J. Virol., 56, 135–143, 1985) and was obtained from Ed Mocarski, Stanford University. pON-CMVIE, described earlier, contains the PstI/SocII fragment of the human cytomegalovirus major immediate early promoter in pON1.

Sequences from the feline leukemia virus A subgroup (strain Glasgow-1 genome are cloned in the plasmid pFGA-5, obtained from Dr. James Neil, University of Glasgow. The construction of this clone, its restriction enzyme cleavage map, and relevant DNA sequence is described in Stewart, et al., J. Virol., 58, 825–834, 1986. The env gene was isolated as a PstI/PstI fragment, inserted into pUC19 (Pharmacia, Piscataway, N.J.) to obtain convenient flanking restriction sites (XbaI on the 5'-end, SphI, which can be made blunt with T4 DNA polymerase, on the 3'-end). Plasmid pCMVIE-LeLVenv was made by replacing the beta-galactosidase gene of pON-IECMV with FeLV env.

The CMF promoter—FeLV env expression cassette was removed from pCMVIE-FELVenv and inserted into the tk insertion vector pGC113 (Example 1) to give plasmid pGC114. This plasmid contains the env transcription unit in the same orientation as the FHV tk gene. This plasmid was co-transfected with FHV UT88-1729 DNA into CRFK cells, and araT resistant plaques selected, as described above. The resulting virus was called FHV-114. FHV 114 directs expression of FeLV gp85 in infected CRFK cells, as determined by Western blotting or immunoprecipitation with various anti-FeLV monoclonal or polyclonal antisera (obtained from Dr. Niels Pedersen, U. California, Davis). Intranasal administration of this virus to cats was found to induce antibodies to FeLV.

EXAMPLE 3

Vaccination of Cats with Recombinant FHV Vaccine

FHVΔ113 as unformulated material, i.e., medium from cells infected with FHVΔ113, was administered to cats by intranasal inoculation. Unlike the parent virus UT88-1729, which caused severe or even/lethal disease, the FHVΔ113-inoculated cats did not show signs of illness. These cats developed antibodies that neutralized FHV. When these cats were challenged with virulent FHV strains, they did not develop respiratory symptoms as did unvaccinated cats. This demonstrates that thymidine kinase negative FHVs are avirulent and raise a protective immune response, neither of which was known before this invention.

Those skilled in the art will recognize, in light of the present disclosure, that the methods of the claimed invention can be carried out in a variety of ways. The exemplifications of the invention described above merely illustrate the invention and in no way limit the scope of the accompanying claims. Other modifications of the above-described embodiments of the invention that are obvious to those skilled in the art are intended to be within the scope of the following claims. Particularly well known are methods for formulating and administering vaccines comprising live attenuated viruses such as those of the instant invention.

We claim:

1. A recombinant DNA molecule comprising a feline herpes virus thymidine kinase-encoding DNA.

2. The recombinant DNA molecule of claim 1 wherein the thymidine kinase-encoding DNA comprises the following DNA sequence:

```
                                                5'-AT GGCGAGTGGA
ACCATCCCCG TTCAGAATGA AGAGATTATT AAATCACAGG TGAATACTGT
CCGCATTTAC ATAGATGGTG CCTATGGAAT AGGTAAGAGT TTAACGGCGA
AGTACCTGGT CAGAGCGGAT GAAAATCGAC CGGGATATAC TTACTACTTC
CCAGAACCAA TGCTATACTG GCGTAGTCTC TTTGAAACTG ATGTTGTCGG
TGGTATCTAT GCCGTCCAGG ACCGGAAACG ACGTGGTGAA TTATCAGCTG
AAGATGCTGC CTATATCACC GCCCACTATC AAGCAAGATT TGCCGCACCA
TACCTTCTTT TACATTCCAG ACTATCCACA ATAACAGGAT ATCAGAAAGT
TGTATGTGAG GAACACCCCG ACGTGACCCT AATCATAGAT AGACACCCTC
TCGCCTCTCT GGTCTGTTTC CCACTCGCAA GATATTTTGT GGGTGATATG
ACTCTTGGGT CTGTACTTAG TCTAATGGCA ACACTTCCAC GAGAACCTCC
TGGTGGAAAT CTAGTTGTAA CAACCTTGAA TATCGAGGAA CATTTGAAGC
GTCTCAGGGG ACGCTCAAGA ACCGGAGAAC AGATAGACAT GAAGCTAATT
```

-continued

```
CACGCACTAC GCAATGTATA TATGATGTTG GTACATACTA AGAAATTTTT

AACAAAAAAT ACTAGTTGGC GTGATGGGTG GGGGAAGCTT AAAATTTTCT

CCCACTATGA ACGGAATAGG CTCGTGGAAA CTACAATAGT TTCCGATTCG

ACGGAGTCAG ATTTATGTGA CACATTATTC AGTGTTTTCA AAGCCCGGGA

GCTCTCCGAC CAAAATGGAG ATCTACTTGA CATGCATGCA TGGGTCCTCG

ATGGACTTAT GGAAACCCTC CAAAATTTAC AGATCTTTAC TTTAAATCTG

GAAGGAACCC CTGATGAATG TGCCGCCGCC TTGGGAGCAC TGAGACAAGA

TATGGATATG ACATTTATAG CCGCATGTGA TATGCACCGT ATAAGTGAAG

CCTTGACGAT ATACCATTAA-3'.
```

3. The recombinant DNA molecule of claim 2 wherein the DNA sequence is:

```
5'-GTATAACCAC AGATCTGTAT GTTCAACCTC ACGACGTTGA TGTCTTACTA

GTGTATCCAT ATTTTGAAAA CGACACGTTT TCAGCTCAAT TAGAAAACAT

ATACCACCCC CTTCTCCCTC AAATTGTATA GTACATACAC AATCAGTCGG

CGACGACCCA AGTTAACCTC ACATGCTAGG TACACGCCCT TAGCCTTTTT

AAGAGACTCT GCGGATACAG AGCCGCCCAA TAAACACTCG AGTCGGTCGG

TATATACTCC ACTCGCAGAG GTCGAGGATA TATCGCGCTT GAGGACAGCA

TAAAAGCGAT TGTGGNATCG AATTCCAGCC CGGAGCCTCA ATCCGACACT

GCGTCGTTGT TCACGTTTCA TCATACACAG ATCAGACGAT GGCGAGTGGA

ACCATCCCCG TTCAGAATGA AGAGATTATT AAATCACAGG TGAATACTGT

CCGCATTTAC ATAGATGGTG CCTATGGAAT AGGTAAGAGT TAACGGCGA

AGTACCTGGT CAGAGCGGAT GAAAATCGAC CGGGATATAC TTACTACTTC

CCAGAACCAA TGCTATACTG GCGTAGTCTC TTTGAAACTG ATGTTGTCGG

TGGTATCTAT GCCGTCCAGG ACCGGAAACG ACGTGGTGAA TTATCAGCTG

AAGATGCTGC CTATATCACC GCCCACTATC AAGCAAGATT TGCCGCACCA

TACCTTCTTT TACATTCCAG ACTATCCACA ATAACAGGAT ATCAGAAAGT

TGTATGTGAG GAACACCCCG ACGTGACCCT AATCATAGAT AGACACCCTC

TCGCCTCTCT GGTCTGTTTC CCACTCGCAA GATATTTTGT GGGTGATATG

ACTCTTGGGT CTGTACTTAG TCTAATGGCA ACACTTCCAC GAGAACCTCC

TGGTGGAAAT CTAGTTGTAA CAACCTTGAA TATCGAGGAA CATTTGAAGC

GTCTCAGGGG ACGCTCAAGA ACCGGAGAAC AGATAGACAT GAAGCTAATT

CACGCACTAC GCAATGTATA TATGATGTTG GTACATACTA AGAAATTTTT

AACAAAAAAT ACTAGTTGGC GTGATGGGTG GGGGAAGCTT AAAATTTTCT

CCCACTATGA ACGGAATAGG CTCGTGGAAA CTACAATAGT TTCCGATTCG

ACGGAGTCAG ATTTATGTGA CACATTATTC AGTGTTTTCA AAGCCCGGGA

GCTCTCCGAC CAAAATGGAG ATCTACTTGA CATGCATGCA TGGGTCCTCG

ATGGACTTAT GGAAACCCTC CAAAATTTAC AGATCTTTAC TTTAAATCTG

GAAGGAACCC CTGATGAATG TGCCGCCGCC TTGGGAGCAC TGAGACAAGA

TATGGATATG ACATTTATAG CCGCATGTGA TATGCACCGT ATAAGTGAAG

CCTTGACGAT ATACCATTAA ACATTAGTGG TGTTCCCTAT TACCCCCCTG

TGGTGAATGT GTGGAGGTCA GGGGATAATT GTATAATGAC CATCGTTTCA
```

```
TGAATAAAAT AACCGTGTGT GATGTGGATG TATTCATTAA TTGAATTTCT

CTTCCGGTTT TAGATCTTTA TAAGCGTAAA ACTGGTGTTT TAAATCCAAG

AGCCGGGTTC TTTGGAGGTT GGTCACATCA TCGCCACAGC CCGTGGATTC

AAGCAATCTT ATGATGTGTT TGATAATATA CCTATCGATA TTCCTGATCA

TTGTATCGAG GATGTTGACT GGTTACCGAT GATGGATAGA CCTGATGAGG

TGGCTGG-3.
```

4. A feline herpes virus thymidine kinase-encoding DNA sequence that encodes the amino acid residue sequence, depicted from the amino to carboxy terminus:

| | | | | |
|---|---|---|---|---|
| MASGTIPVQN | EEIIKSQVNT | VRIYIDGAYG | IGKSLTAKYL | VRADENRPGY |
| TYYFPEPMLY | WRSLFETDVV | GGIYAVQDRK | RRGELSAEDA | AYITAHYQAR |
| FAAPYLLLHS | RLSTITGYQK | VVCEEHPDVT | LIIDRHPLAS | LVCFPLARYF |
| VGDMTLGSVL | SLMATLPREP | PGGNLVVTTL | NIEEHLKRLR | GRSTRGEQID |
| MKLIHALRNV | YMMLVHTKKF | LTKNTSWRDG | WGKLKIFSHY | ERNRLVETTI |
| VSDSTESDLC | DTLFSVFKAR | ELSDQNGDLL | DMHAWVLDGL | METLQNLQIF |
| TLNLEGTPDE | CAAALGALRQ | DMDMTFIAAC | DMHRISEALT | IYH | wherein, Alanine is A, Arginine is R, Asparagine is N, Aspartic acid is D, Cysteine is C, Glutamine is Q, Glutamic acid is E. Glycine is G, Histidine is H, Isoleucine is I, Leucine is L, Lysine is K, Methionine is M, Phenylalanine is F, Proline is P, Serine is S, Threonine is T, Tryptophan is W, Tryosine is Y, and Valine is V.

5. Recombinant thymidine kinase-negative feline herpes virus.

6. A recombinant thymidine kinase-negative feline herpes virus according to claim 5 comprising a nonfunctional thymidine-kinase gene comprising a portion of the DNA sequence of claim 3.

7. The recombinant feline herpes virus of claim 5 that further comprises an expression cassette that comprises a promoter that can drive expression of a gene product in feline herpes virus-infected cells and a coding sequence positioned for expression from said promoter.

8. A vaccine comprising thymidine kinase-negative feline herpes virus of claim 5.

9. A vaccine comprising the thymidine kinase-negative feline herpes virus of claim 6.

10. The recombinant feline herpes virus of claim 7, wherein said promoter is a herpes virus promoter.

11. The recombinant feline herpes virus of claim 7, wherein said coding sequence encodes a viral gene product.

12. A vaccine comprising the recombinant feline herpes virus of claim 7.

13. The recombinant feline herpes virus of claim 10, wherein said promoter is selected from the group consisting of the herpes simplex alpha-4, cytomegalovirus immediate early, and feline herpes virus thymidine kinase promoters.

14. The recombinant feline herpes virus of claim 13, wherein said promoter is the cytomegalovirus immediate early promoter.

15. The recombinant feline herpes virus of claim 11 wherein said gene product is selected from the group consisting of feline leukemia virus, feline infectious peritonitis (FIP) virus, calicivirus, rabies virus, feline immunodeficiency virus (FIV), feline parvovirus (panleukopenia virus), and feline Chlamydia.

16. The recombinant feline herpes virus of claim 11, wherein said viral gene product is a gene product of feline leukemia virus.

17. The recombinant feline herpes virus of claim 16, wherein said gene product is selected from the envelope, gag, and pol gene products.

18. The recombinant feline herpes virus of claim 17, wherein said gene product is a secreted envelope gene product.

19. A vaccine comprising the recombinant feline herpes virus of claim 18.

20. A recombinant DNA molecule that comprises the thymidine kinase gene promoter of feline herpes virus.

21. The recombinant DNA molecule of claim 20 that comprises the DNA sequence:

```
5'-CAATAAACACTCGAGTCGGTCG-
GTATATACTCCACTCGCAGAGGTCGAG-
GATATAT.
```

22. The recombinant DNA molecule of claim 21 that comprises the DNA sequence:

```
5'-GTATAACCAC AGATCTGTAT GTTCAACCTC ACGACGTTGA TGTCTTACTA

GTGTATCCAT ATTTTGAAAA CGACACGTTT TCAGCTCAAT TAGAAAACAT

ATACCACCCC CTTCTCCCTC AAATTGTATA GTACATACAC AATCAGTCGG

CGACGACCCA AGTTAACCTC ACATGCTAGG TACACGCCCT TAGCCTTTTT

AAGAGACTCT GCGGATACAG AGCCGCCCAA TAAACACTCG AGTCGGTCGG
```

-continued

```
TATATACTCC ACTCGCAGAG GTCGAGGATA TATCGCGCTT GAGGACAGCA
TAAAAGCGAT TGTGGNATCG AATTCCAGCC CGGAGCCTCA ATCCGACACT
GCGTCGTTGT TCACGTTTCA TCATACACAG TCAGACG-3'.
```

* * * * *

UNITED STATES PATENT AND TRADEMARK OFFICE
CERTIFICATE OF CORRECTION

PATENT NO. : 5,324,664                                   Page 1 of 3
DATED     : June 28, 1994
INVENTOR(S) : Jack H. Nunberg, et al It is certified that error appears in the above-indentified patent and that said Letters Patent is hereby corrected as shown below:

On title page, item [54] and col. 1, line 1, "THYMIDIEN" should read
--THYMIDINE--
        Column 2, the Attorney, Agent, or Firm "James D. Darnely, Jr." should read -- James D. Darnley, Jr. --

Column 1, line 38, "rhinotrachetitis" should read -- rhinotracheitis --

Column 1, line 43, "DNA encodes" should read -- DNA that encodes --

Column 1, line 65, "Tymidine" should read -- Thymidine --

Column 2, line 59, "thymidinekinase-encoding" should read -- thymidine kinase-encoding --

Column 3, line 26, "produce in earlier" should read -- produced in earlier --

Column 6, line 12, "genetic doe)." should read -- genetic code). --

Column 6, line 21, "Nos. 4,683,193" should read -- Nos. 4,683,195 --

Column 6, line 27, "To silate the" should read -- To isolate the --

Column 6, line 37, "(US-D strain" should read -- (UC-D strain --

Column 7, line 15, "form the gel" should read -- from the gel --

Column 8, line 13, "However, using" should read -- However, by using --

Column 8, line 31, "Underlines" should read -- Underlined --

UNITED STATES PATENT AND TRADEMARK OFFICE
CERTIFICATE OF CORRECTION

PATENT NO. : 5,324,664
DATED : June 28, 1994
INVENTOR(S) : Jack H. Nunberg, et al It is certified that error appears in the above-indentified patent and that said Letters Patent is hereby corrected as shown below:

Column 10, line 47, "though the use" should read -- through the use --

Column 12, line 63, "13301" should read -- 12301 --

Column 12, line 63, "Drie," should read -- Drive, --

Column 13, line 17, "CMF" should read -- CMV --

Column 13, line 35, "descried" should read -- described --

Column 13, line 53, "Lose" should read -- Lowe --

Column 14, line 21, "Tis" should read -- This --

Column 14, line 38, "ter/eta-" should read -- ter/beta- --

Column 16, line 11, "$lysin_{234}$" should read -- $lysine_{234}$ --

Column 16, line 33, "345 pb" should read -- 345 bp --

UNITED STATES PATENT AND TRADEMARK OFFICE
CERTIFICATE OF CORRECTION

PATENT NO. : 5,324,664
DATED : June 28, 1994
INVENTOR(S) : Jack H. Nunberg, et al It is certified that error appears in the above-indentified patent and that said Letters Patent is hereby corrected as shown below:

Column 17, line 42, "pCMVIE-LeL-" should read -- pCMVIE-FeL- --

Column 21/22, in Claim 4, line 23, "GRSTRGEQID" should read -- GRSRTGEQID --

Signed and Sealed this

Twentieth Day of December, 1994

BRUCE LEHMAN

*Attest:*

*Attesting Officer*    *Commissioner of Patents and Trademarks*